(12) United States Patent
Nakamoto et al.

(10) Patent No.: US 9,377,786 B2
(45) Date of Patent: Jun. 28, 2016

(54) ODOR GENERATOR

(75) Inventors: Takamichi Nakamoto, Tokyo (JP); Yossiri Ariyakul, Tokyo (JP)

(73) Assignees: Tokyo Institute of Technology, Tokyo (JP); Toppan Printing Co., Ltd., Tokyo (JP)

( * ) Notice: Subject to any disclaimer, the term of this patent is extended or adjusted under 35 U.S.C. 154(b) by 908 days.

(21) Appl. No.: 13/582,631

(22) PCT Filed: Mar. 2, 2011

(86) PCT No.: PCT/JP2011/054790
§ 371 (c)(1),
(2), (4) Date: Sep. 4, 2012

(87) PCT Pub. No.: WO2011/108604
PCT Pub. Date: Sep. 9, 2011

(65) Prior Publication Data
US 2012/0325941 A1 Dec. 27, 2012

(30) Foreign Application Priority Data
Mar. 4, 2010 (JP) .................................. 2010-048365

(51) Int. Cl.
G05D 11/13 (2006.01)
A61L 9/12 (2006.01)
A61L 9/14 (2006.01)
A41G 1/00 (2006.01)

(52) U.S. Cl.
CPC .............. *G05D 11/132* (2013.01); *A61L 9/122* (2013.01); *A61L 9/125* (2013.01); *A61L 9/14* (2013.01); *A41G 1/006* (2013.01); *A61L 2209/111* (2013.01); *A61L 2209/135* (2013.01)

(58) Field of Classification Search
CPC .............. F23D 11/32; A61L 2209/135; A61L 2209/111; A61L 9/122; A61L 9/125
USPC ....................................................... 239/102.1
See application file for complete search history.

(56) References Cited

U.S. PATENT DOCUMENTS

| 3,923,426 | A | * | 12/1975 | Theeuwes | F04B 17/003 |
| | | | | | 204/630 |
| 4,689,515 | A | * | 8/1987 | Benndorf | B05B 17/0623 |
| | | | | | 239/102.2 |
| 4,735,358 | A | * | 4/1988 | Morita | A01M 1/2072 |
| | | | | | 206/389 |
| 4,752,422 | A | * | 6/1988 | Uchida | A61L 9/122 |
| | | | | | 239/58 |

(Continued)

FOREIGN PATENT DOCUMENTS

JP      05215357 A   8/1993
JP    2005525897 A   9/2005

(Continued)

*Primary Examiner* — Arthur O Hall
*Assistant Examiner* — Chee-Chong Lee
(74) *Attorney, Agent, or Firm* — Capitol City TechLaw, PLLC; Samuel P. Burkholder

(57) ABSTRACT

The present invention provides an odor generator capable of providing a wide range of odors including the odor of a low volatile fragrance ingredient. The odor generator comprises a plurality of electroosmotic flow pumps, each of which typically includes a storage section for storing a liquid containing a volatile fragrance ingredient, and an outlet section having a porous material arranged for discharging the stored liquid through the porous material when a voltage is applied to the porous material and a surface acoustic wave (SAW) or other element for atomizing or vaporizing the liquid discharged from the outlet section.

2 Claims, 8 Drawing Sheets

(56) References Cited

U.S. PATENT DOCUMENTS

| | | | |
|---|---|---|---|
| 5,724,256 A | 3/1998 | Lee et al. | |
| 6,105,877 A * | 8/2000 | Coffee | A61M 15/02 128/204.21 |
| 6,595,208 B1 * | 7/2003 | Coffee | B05B 5/002 128/200.14 |
| 6,994,328 B2 * | 2/2006 | Watkins | A61L 9/122 239/102.1 |
| 2005/0185392 A1 | 8/2005 | Walter et al. | |
| 2009/0133764 A1 | 5/2009 | Nakamoto et al. | |

FOREIGN PATENT DOCUMENTS

| | | | |
|---|---|---|---|
| JP | 2007106626 A | 4/2007 | |
| JP | 3955954 B2 | 8/2007 | |
| JP | WO2007/122879 * | 11/2007 | G01N 5/02 |
| WO | 2007122879 A1 | 11/2007 | |

* cited by examiner

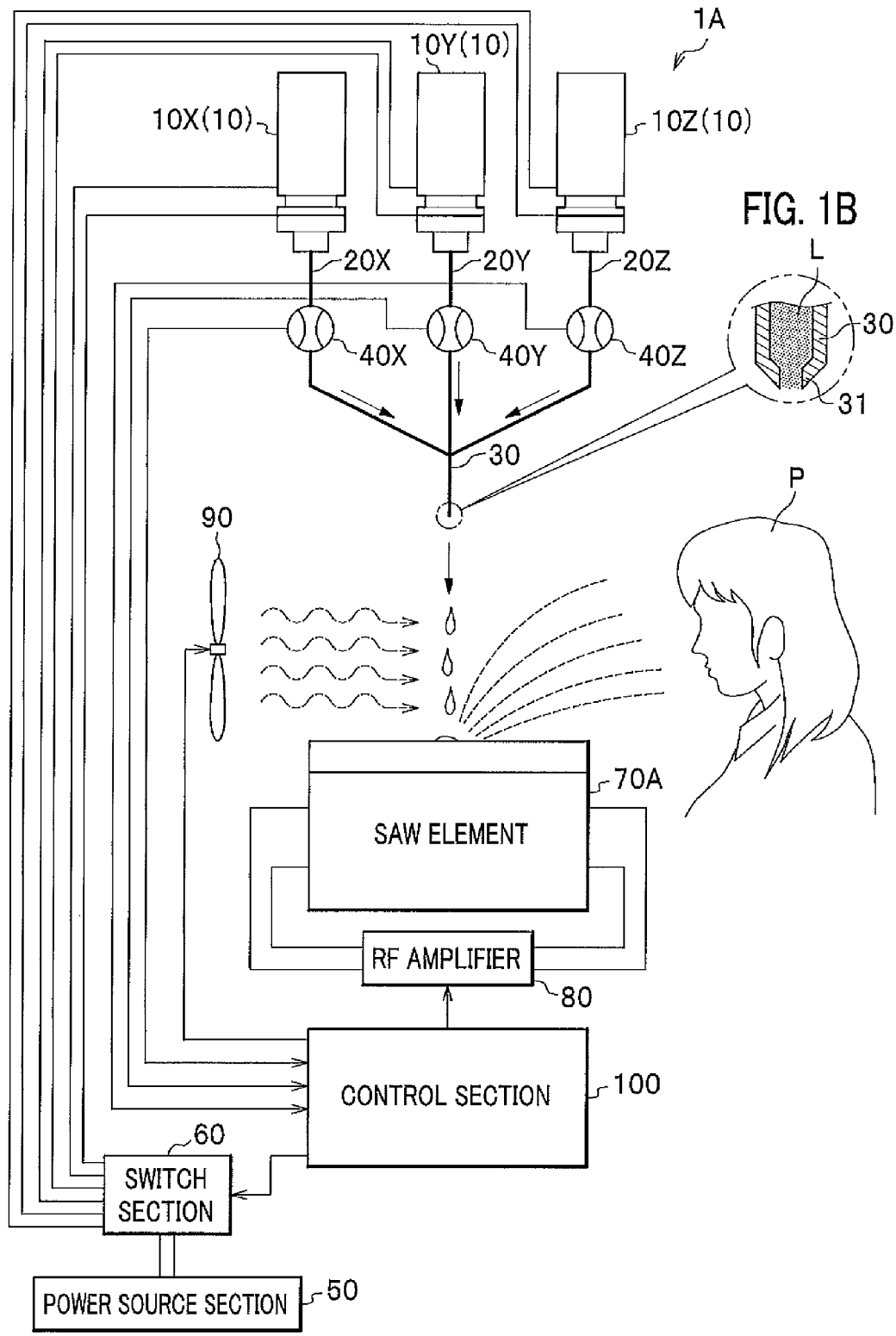

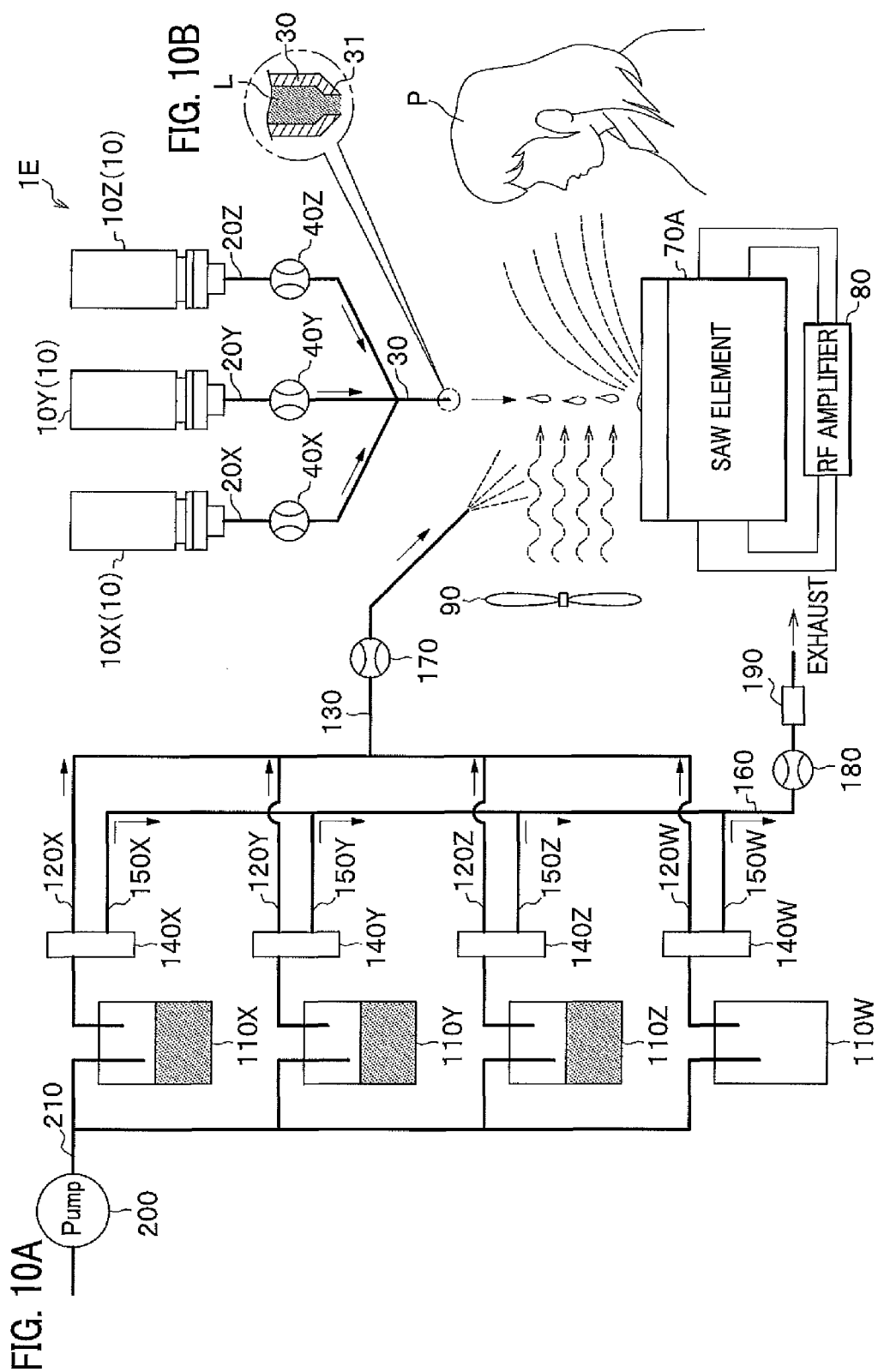

ODOR GENERATOR

TECHNICAL FIELD

The present invention relates to an odor generator.

BACKGROUND ART

In recent years, attempts have been begun in the field of virtual reality to provide olfactory information for users. Int'l. Pat. Appl. No. WO/2007/122879, published Jan. 11, 2007, the contents of which are incorporated herein by reference, discloses an odor blender (olfactory display) including component odor gas containers storing component odor gases, pipes connected to the component odor gas containers, solenoid valves disposed on the pipes to be opened and closed to blend the component gases in desired quantities for producing a desired odor.

BRIEF SUMMARY

Performances of such a known odor blender, however, are not good enough to provide the odor of a low volatile fragrance ingredient for the users. The low volatile fragrance ingredient is an ingredient essential to the olfactory display because even a low content of the ingredient provides an odor perceptible to the users.

The present invention has been made under the above circumstances, and it is an object of the present invention to provide an odor generator capable of providing a wide range of odors including the odor of a low volatile fragrance ingredient.

To solve the above problem, the present invention provides an odor generator comprising: an electroosmotic flow pump including: a storage section for storing a liquid containing a volatile fragrance ingredient, and an outlet section having a porous material therein for discharging the stored liquid to the outside through the porous material when a voltage is applied to the porous material; and an atomizing or vaporizing section for atomizing or vaporizing the liquid discharged from the outlet section.

With the above configuration, the odor generator according to the present invention has the atomizing or vaporizing section which forces the volatile fragrance ingredient to volatilize. Therefore, the odor generator is capable of more easily providing the low volatile fragrance ingredient for the user than conventional techniques that leave a fragrance ingredient to spontaneously volatilize. Further, the odor generator has the electroosmotic flow pump with the built-in storage section. Therefore, the odor generator can be made compact, is operable even with bubbles in the liquid, and facilitates the construction of its liquid circuit.

The atomizing or vaporizing section may be either a surface acoustic wave element or an ultrasonic vibrator for atomizing the liquid discharged from the outlet section. Alternatively, the atomizing or vaporizing section may be a heater for vaporizing the liquid discharged from the outlet section by heating.

The odor generator may comprise a plurality of electroosmotic flow pumps including the storage sections storing the liquids respectively containing different volatile fragrance ingredients, and further comprise a control section for controlling operations of the plurality of electroosmotic flow pumps. Further, the odor generator may further comprise: a plurality of pipes for the liquids to flow through, which pipes are connected respectively to the outlet sections of the plurality of electroosmotic flow pumps; a merging pipe connected to the plurality of pipes for merging the liquids flowing thereinto and allowing the merged liquids to be discharged to the atomizing or vaporizing section, and a plurality of liquid quantity sensors for detecting quantities of the respective liquids flowing through the plurality of pipes, wherein the control section controls the operations of the plurality of electroosmotic flow pumps by feedback of detection results from the plurality of liquid quantity sensors.

Still further, the odor generator may further comprise: a second storage section for storing a liquid or a solid containing a volatile fragrance ingredient; a pump for supplying the air to the second storage section; a second pipe connected to the second storage section for a gas inside the second storage section to flow through; and a three-way valve disposed on the second pipe and operable to be switched between a first state in which the three-way valve discharges the gas to a position where the gas joins the liquid or liquids atomized or vaporized by the atomizing or vaporizing section, and a second state in which the three-way valve exhausts the gas into a bypath.

Effect of the Invention

The present invention is capable of providing a wide range of odors including the odor of a low volatile fragrance ingredient.

BRIEF DESCRIPTION OF THE DRAWINGS

FIG. 1A is a schematic diagram of an odor generator according to a first embodiment of the present invention, and FIG. 1B is a cross section diagram of a merging pipe.

FIG. 10A is a schematic diagram of the odor generator according to a fourth embodiment of the present invention, and FIG. 10B is a cross section diagram of a merging pipe.

DETAILED DESCRIPTION

Figure 2A:
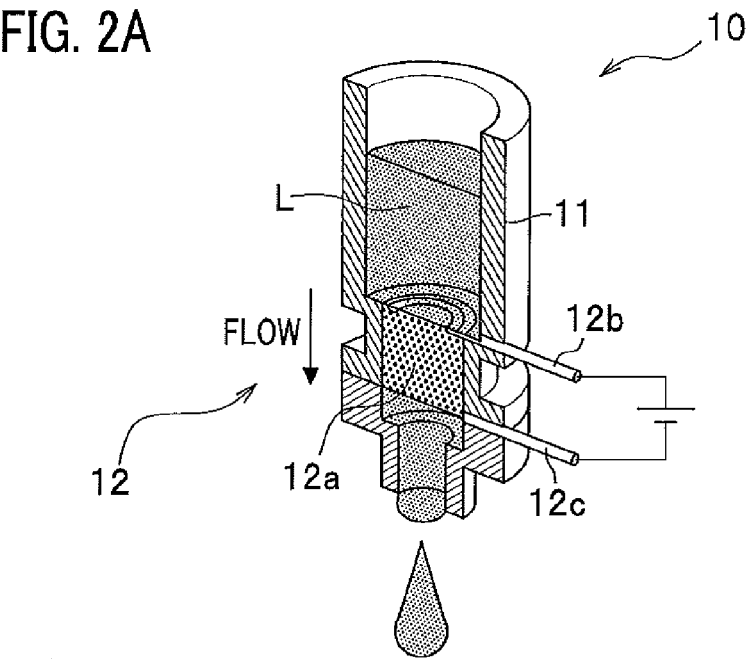
FIG. 2A is a cross section diagram of an electroosmotic flow pump of FIGS. 1A and 1B.

In the following paragraphs, embodiments of the present invention will be described with reference to the drawings as required. Like components are denoted by like reference numerals and will not be described in further detail.

First Embodiment

Figure 2B:
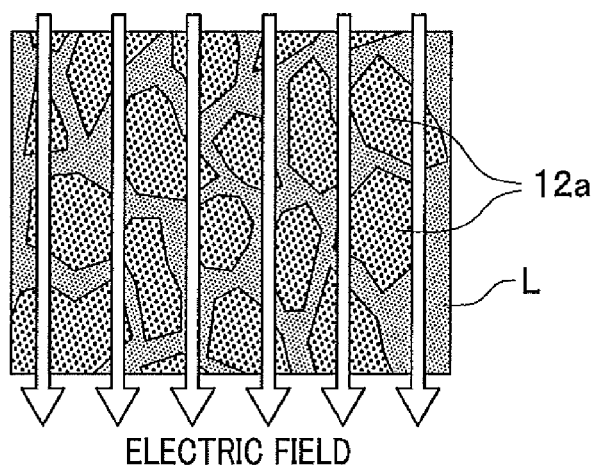
FIG. 2B is a partially enlarged view of FIG. 2A.
Figure 2C:
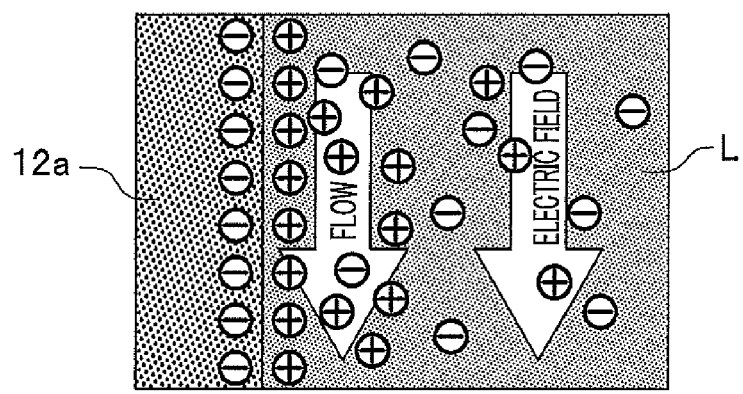
FIG. 2C is a partially enlarged view of FIG. 2B.

Now, description will be made of an odor generator according to a first embodiment of the present invention with reference to FIGS. 1A, 1B and 2A-2C. FIG. 1A is a schematic diagram of the odor generator according to the first embodiment of the present invention, and FIG. 1B is a cross section diagram of a merging pipe. FIG. 2A is a cross section diagram of an electroosmotic flow pump of FIGS. 1A and 1B, FIG. 2B is a partially enlarged view of FIG. 2A, and FIG. 2C is a partially enlarged view of FIG. 2B.

As shown in FIG. 1A, an odor generator 1A according to a first embodiment of the present invention includes a plurality of electroosmotic flow pumps 10 (10X, 10Y, 10Z), a plurality of pipes 20X, 20Y, 20Z, a merging pipe 30, a plurality of liquid quantity sensors 40X, 40Y, 40Z, a power source section 50, a switch section 60, a surface acoustic wave (SAW: Surface Acoustic Wave) element 70A, an RF (Radio Frequency) amplifier 80, a blowing section 90, and a control section 100.

The plurality of electroosmotic flow pumps 10X, 10Y, 10Z are small pumps of a diameter of approximately 7 mm for discharging a liquid by electroendosmosis, and are capable of developing great discharge pressures (100 kPa or more) even at low drive voltages (for example, 2 to 24 V). According to the present embodiment, the plurality of electroosmotic flow pumps 10X, 10Y, 10Z are controlled by the control section 100 to discharge liquids containing volatile fragrance ingredients onto the SAW element 70A.

As shown in FIG. 2A, the electroosmotic flow pump 10 includes a storage section 11 and an outlet section 12. The outlet section 12 has a porous material 12a and electrodes 12b, 12c. The storage section 11 stores a liquid L containing a volatile fragrance ingredient. The porous material 12a in the outlet section 12 is located beneath the storage section 11. By applying a voltage between the electrodes 12b and 12c, an electric field is created as shown in FIG. 2B to generate a flow of the liquid L through pores (voids) of the porous material 12a and to allow the liquid L to be discharged from the outlet section 12 to the outside.

Referring back to FIG. 1A, the plurality of pipes 20X, 20Y, 20Z are connected to the plurality of electroosmotic flow pumps 10X, 10Y, 10Z, respectively, so that liquids can flow through the plurality of pipes 20X, 20Y, 20Z and the plurality of electroosmotic flow pumps 10X, 10Y, 10Z.

The merging pipe 30 is connected to the plurality of pipes 20X, 20Y, 20Z so that liquids can flow through the plurality of pipes 20X, 20Y, 20Z and the merging pipe 30. The plurality of pipes 20X, 20Y, 20Z and the merging pipe 30 are, for example, stainless steel tubes of an inside diameter of approximately 100 μm. As shown in FIG. 1B, the merging pipe 30 has a tip end provided with an orifice 31 through which the liquid L is discharged in the form of droplets.

The plurality of liquid quantity sensors 40X, 40Y, 40Z are disposed on the plurality of pipes 20X, 20Y, 20Z, respectively, for detecting the quantities of the liquids flowing through the plurality of pipes 20X, 20Y, 20Z and outputting the detection results to the controller 110.

The power source section 50 is a direct-current power source for supplying electric power to the plurality of electroosmotic flow pumps 10X, 10Y, 10Z.

The switch section 60 switches on and off the electrical connection between the power source section 50 and the plurality of electroosmotic flow pumps 10X, 10Y, 10Z.

The SAW element 70A is an example of an atomizing or vaporizing section. The SAW element 70A propagates, through a liquid on the surface thereof, surface acoustic waves which generate, in the liquid, longitudinal waves which atomize the liquid. The SAW element 70A according to the present embodiment is controlled by the control section 100 to atomize the liquids L discharged onto the surface of the SAW element 70A from the plurality of electroosmotic flow pumps 10X, 10Y, 10Z.

The RF amplifier 80 is an amplifier for amplifying an AC voltage (RF burst wave) output from the control section 100 and applying the amplified AC voltage to the SAW element 70A.

The blowing section 90 is a fan for generating the wind to carry to a user P the volatile fragrance ingredients volatilized and released from the atomized liquids L.

The control section 100 is, for example, an FPGA (Field Programmable Gate Array). The FPGA includes a CPU (Central Processing Unit), a RAM (Random Access Memory), a ROM (Read-Only Memory), and an input/output circuit. By switching on and off the switch section 60, the control section 100 controls the operations of the plurality of electroosmotic flow pumps 10X, 10Y, 10Z, applies to the SAW element 70A the AC voltage amplified by the RF amplifier 80, and controls the operation of the blowing section 90. The control section 100 is capable of controlling the operations of the plurality of electroosmotic flow pumps 10X, 10Y, 10Z, of the SAW element 70A and of the blowing section 100, based on signals generated and input into the control section 100 by the user P operating an input section including a keyboard, a mouse, buttons and the like, and based on signals input from an external device into the control section 100.

In the odor generator 1A according to the first embodiment of the present invention, in order to generate and provide a desired odor for the user P, the control section 100 drives the switch section 60 to control the duty ratio of the voltages applied to the electrodes of the plurality of respective electroosmotic flow pumps 10X, 10Y, 10Z and thus adjust the ratio of the volumes of the liquids discharged from the plurality of electroosmotic flow pumps 10X, 10Y, 10Z onto the surface of the SAW element 70A, thereby generating and providing a desired odor for the user P.

Further, the control section 100 controls the magnitude of the voltage applied to the electrodes of the plurality of respective electroosmotic flow pumps 10X, 10Y, 10Z by controlling variable resistances (not shown) of the switch section 60 to adjust the ratio between the volumes of the liquids discharged from the plurality of electroosmotic flow pumps 10X, 10Y, 10Z, thereby generating and providing a desired odor for the user P.

Note that it is possible to replace the plurality of electroosmotic flow pumps 10X, 10Y, 10Z with a plurality of inkjet mechanisms. The inkjet mechanisms require the pressures applied to the liquids to be finely adjusted, and also risk an inconsistent odor because the volatile fragrance ingredients are atomized from discharged liquids L before blended together. Further, the inkjet mechanisms each need to be filled with the liquid L to the top end thereof because the presence of bubbles therein prevents the inkjet mechanism from discharging the liquid L. In contrast, the odor generator 1A according to the first embodiment of the present invention has the merging pipe 30 to blend the plurality of liquids L together, resulting in a consistent odor to be provided for the user P. Further, the odor generator 1A according to the first embodiment of the present invention does not need a priming liquid because the presence of bubbles in the electroosmotic flow pump 10 does not prevent the electroosmotic flow pump 10 from discharging the liquid.

The control section 100 controls the operations of the plurality of electroosmotic flow pumps 10X, 10Y, 10Z by feedback of the detection results from the plurality of liquid quantity sensors 40X, 40Y, 40Z. This configuration diminishes the effect of a negative pressure generated by the flow of the liquid L from one electroosmotic flow pump 10 on the quantity of the liquid L from another electroosmotic flow pump 10.

Figure 3:
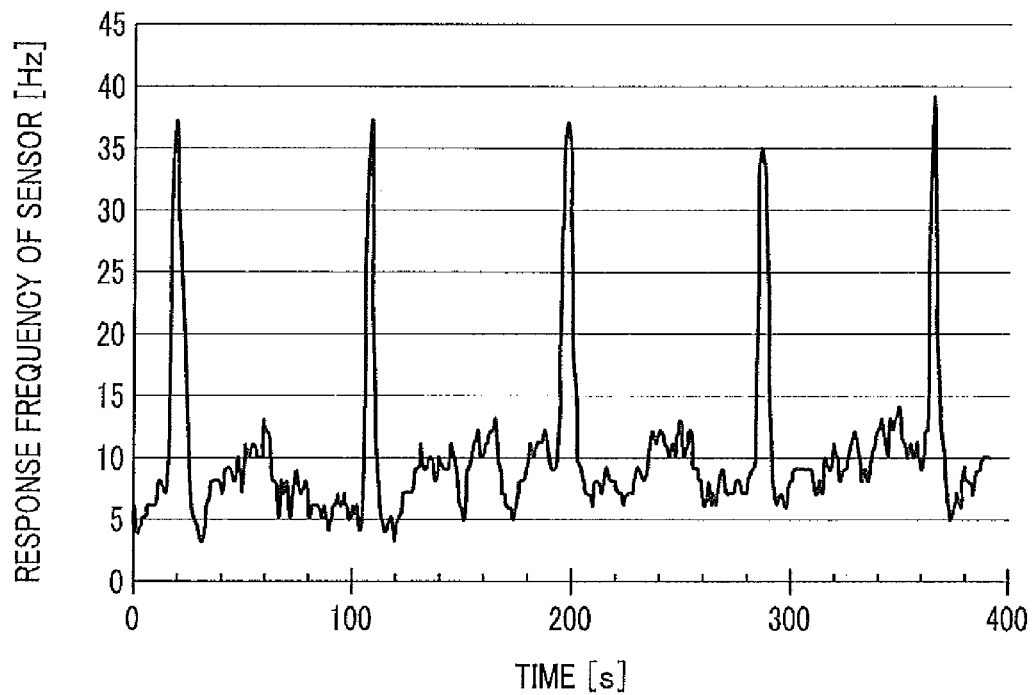
FIG. 3 shows a graph representing the results of detection, by a quartz resonator gas sensor, of an odor generated by the odor generator according to the first embodiment of the present invention.

Now, description will be made of the operation results of the odor generator 1A according to the first embodiment of the present invention with reference to FIG. 3. FIG. 3 shows a graph representing the results of detection, by a quartz resonator gas sensor, of an odor generated by the odor generator according to the first embodiment of the present invention. The operation results of FIG. 3 were produced by atomizing the liquid discharged from one electroosmotic flow pump 10. The odor generator according to the first embodiment of the present invention was operated with the drive voltage of the electroosmotic flow pump 10 of 8 V, the duty ratio of the electroosmotic flow pump 10 of 20%, the frequency of the surface acoustic wave of the SAW element 70A of 61.4 MHz, and the drive voltage of the blowing section 90 of 1.4 V, by using a 10% solution, by volume, of β-ionone as a low volatile fragrance ingredient in ethanol as the liquid L. The control section 100 operates the electroosmotic flow pump 10 for 10 seconds before each of the times of 15, 105, 194, 284, and 364 seconds for the liquid L to be discharged in the form of droplets onto the SAW element 70A and atomized at each of the times of 15, 105, 194, 284, 364 seconds. The quartz resonator gas sensor was a sensor that had an AT-cut quartz oscillator with an oscillation frequency of 20 MHz, and TCP (Tricresyl Phosphate) as a sensing film.

As shown in FIG. 3, the odor generator 1A according to the first embodiment of the present invention is capable of generating an odor immediately after the liquid L is discharged, even when a low volatile fragrance ingredient is involved. Further, the odor generator 1A is capable of stopping the generation of the odor immediately after the discharge of the liquid L is stopped.

Figure 4:
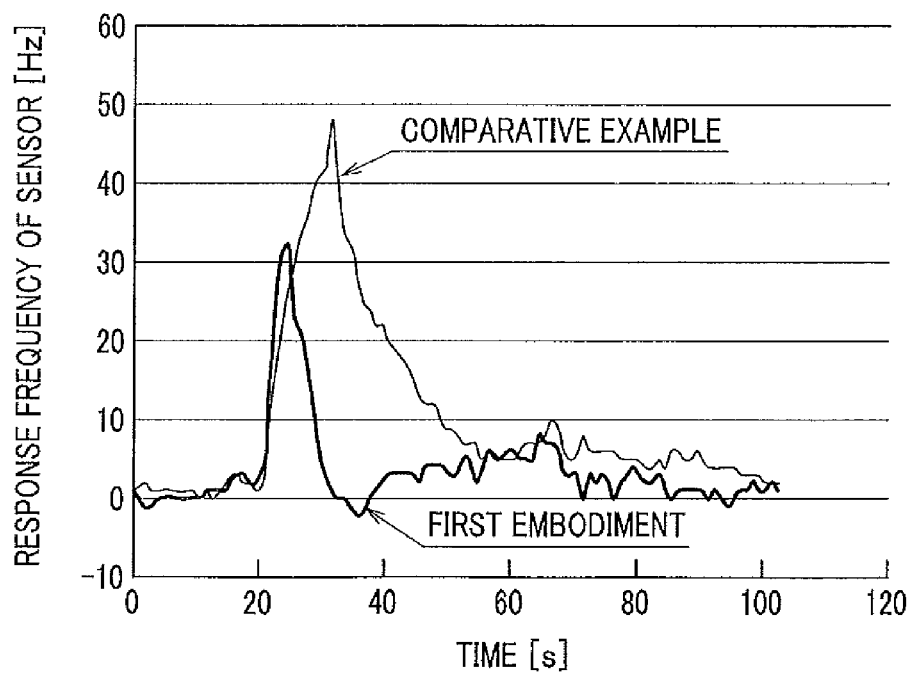
FIG. 4 shows graphs representing the results of detection, by the quartz resonator gas sensor, of the odor generated by the odor generator according to the first embodiment of the present invention and of an odor generated by an odor generator according to Comparative Example.

Now, description will be made of the operation results of an odor generator according to Comparative Example with reference to FIG. 4. FIG. 4 shows graphs representing the results of detection, by the quartz resonator gas sensor, of the odor generated by the odor generator according to the first embodiment of the present invention and of an odor generated by the odor generator according to Comparative Example. The operation results of FIG. 4 of the odor generator according to the first embodiment of the present invention were produced under the same conditions as the operation results of FIG. 3. The operation results of FIG. 4 of the odor generator according to the Comparative Example were produced by using an odor blender of WO/2007/122879 as the odor generator and β-ionone as a low volatile fragrance ingredient. The quartz resonator gas sensor was the same sensor as used to produce the operation results of FIG. 3 that had an AT-cut quartz oscillator with an oscillation frequency of 20 MHz and TCP (Tricresyl Phosphate) as a sensing film. As for the operation results of FIG. 4 of the odor generator 1A according to the first embodiment, the electroosmotic flow pump 10 was operated for 10 seconds before the time of 20 seconds for the liquid L to be discharged in the form of droplets onto the SAW element 70A and atomized at the time of 20 seconds. Also, as for the operation results of FIG. 4, the odor generator according to the Comparative Example opened a solenoid valve at the time of 20 seconds and kept it opened for 10 seconds so that the β-ionone atomized inside the component odor gas container was discharged toward the quartz resonator gas sensor.

FIG. 4 indicates that the odor generator according to Comparative Example was unsuitable for practical use when a low volatile fragrance ingredient was involved because it required too long a time for the intensity of the odor of the low volatile fragrance ingredient to reach a peak after it started being provided (after the quartz resonator gas sensor started detecting the odor) and also because it required too long a time for the once provided odor to disperse.

The odor generator 1A according to the first embodiment of the present invention that has the SAW element 70A, which forces a low volatile fragrance ingredient to volatilize, is capable of more easily providing the low volatile fragrance ingredient for the user P than conventional techniques that leave a fragrance ingredient to spontaneously volatilize.

Further, the odor generator 1A according to the first embodiment of the present invention that has the electroosmotic flow pump 10 with the built-in storage section 11 can be made compact so as to be placed under the nose of the user P. Still further, the odor generator 1A is operable even with bubbles in the liquid L. Moreover, the odor generator 1A facilitates the construction of its liquid circuit.

Moreover, the odor generator 1A according to the first embodiment of the present invention is capable of generating an odor immediately after the liquid L is discharged, even when a low volatile fragrance ingredient is involved. Further, the odor generator 1A is capable of stopping the generation of the odor immediately after the discharge of the liquid L is stopped.

Further, as compared with conventional techniques that use a heater to vaporize the liquid L (which requires time for heating) as described later, the odor generator 1A according to the first embodiment of the present invention that has the SAW element 70A to atomize the liquid L is advantageous with the capability of saving power consumption and the capability of atomizing the liquid L and generating an odor sooner.

Still further, the odor generator 1A according to the first embodiment of the present invention that has the SAW element 70A to atomize the liquid L is capable of properly atomizing only the liquid L on the surface of the SAW element 70A without any thermal effect on the surrounding environment.

Second Embodiment

Figure 5:
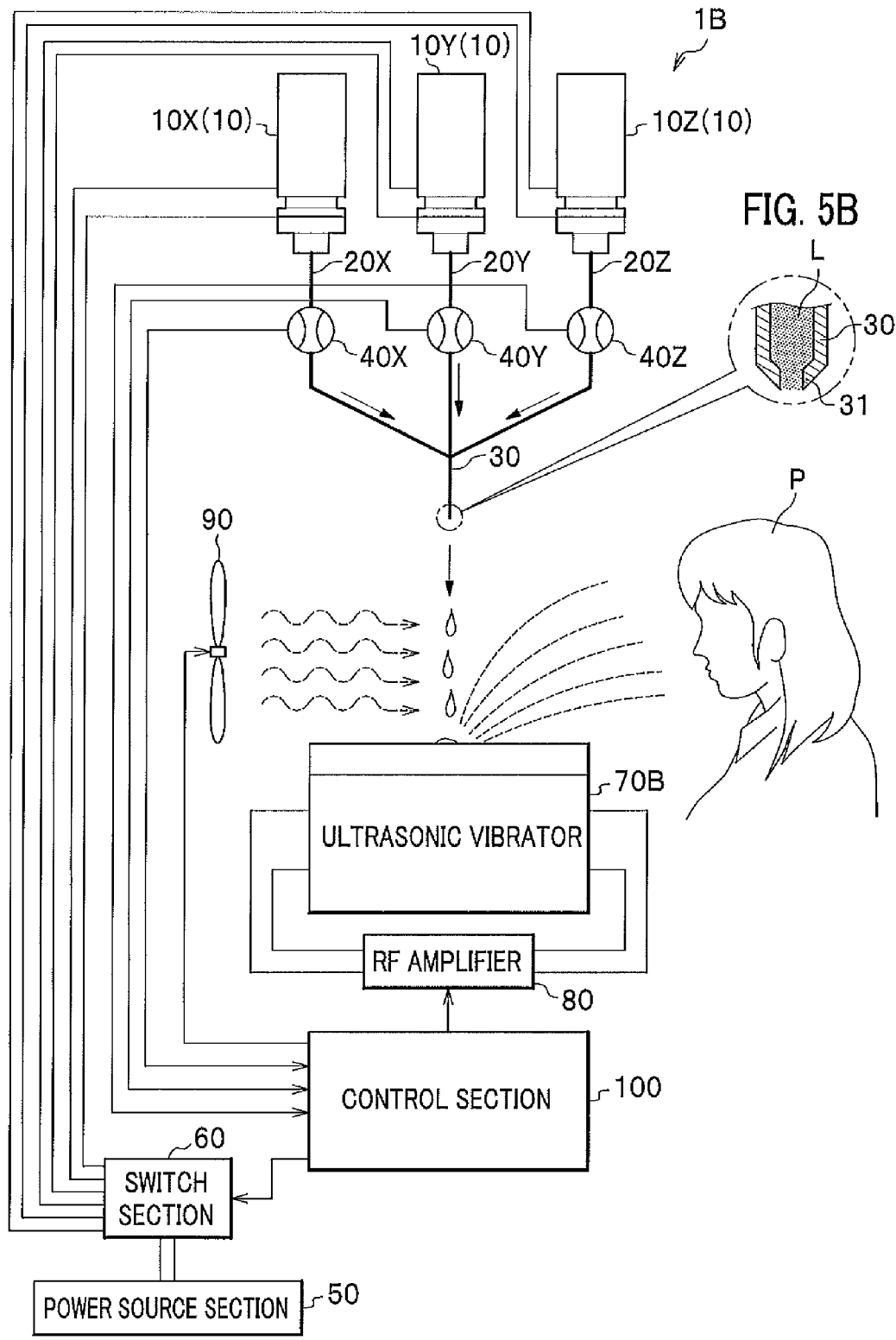
FIG. 5A is a schematic diagram of an odor generator according to a second embodiment of the present invention.
FIG. 5B is a cross section diagram of a merging pipe.

Now, description will be made of an odor generator according to a second embodiment of the present invention, with focus mainly on differences between the odor generator according to the second embodiment and the odor generator 1A according to the first embodiment, with reference to FIGS. 5A and 5B. FIG. 5A is a schematic diagram of the odor generator according to the second embodiment of the present invention, and FIG. 5B is a cross section diagram of a merging pipe.

As shown in FIG. 5A, an odor generator 1B according to a second embodiment of the present invention includes an ultrasonic vibrator 70B in place of the SAW element 70A.

The ultrasonic vibrator 70B is an example of the atomizing or vaporizing section. The ultrasonic vibrator 70B propagates, through a liquid on the surface thereof, ultrasonic waves which generate, in the liquid, vibrations which atomize the liquid. The ultrasonic vibrator 70B according to the present embodiment is controlled by the control section 100 to atomize the liquids L discharged onto the surface of the ultrasonic vibrator 70B from the plurality of electroosmotic flow pumps 10X, 10Y, 10Z. The volatile fragrance ingredients volatilized and released from the vaporized liquids L are carried to the user P by the wind generated by the blowing section 90.

The odor generator 1B according to the second embodiment of the present invention has the same effects as the odor generator 1A according to the first embodiment.

Third Embodiment

Figure 6:
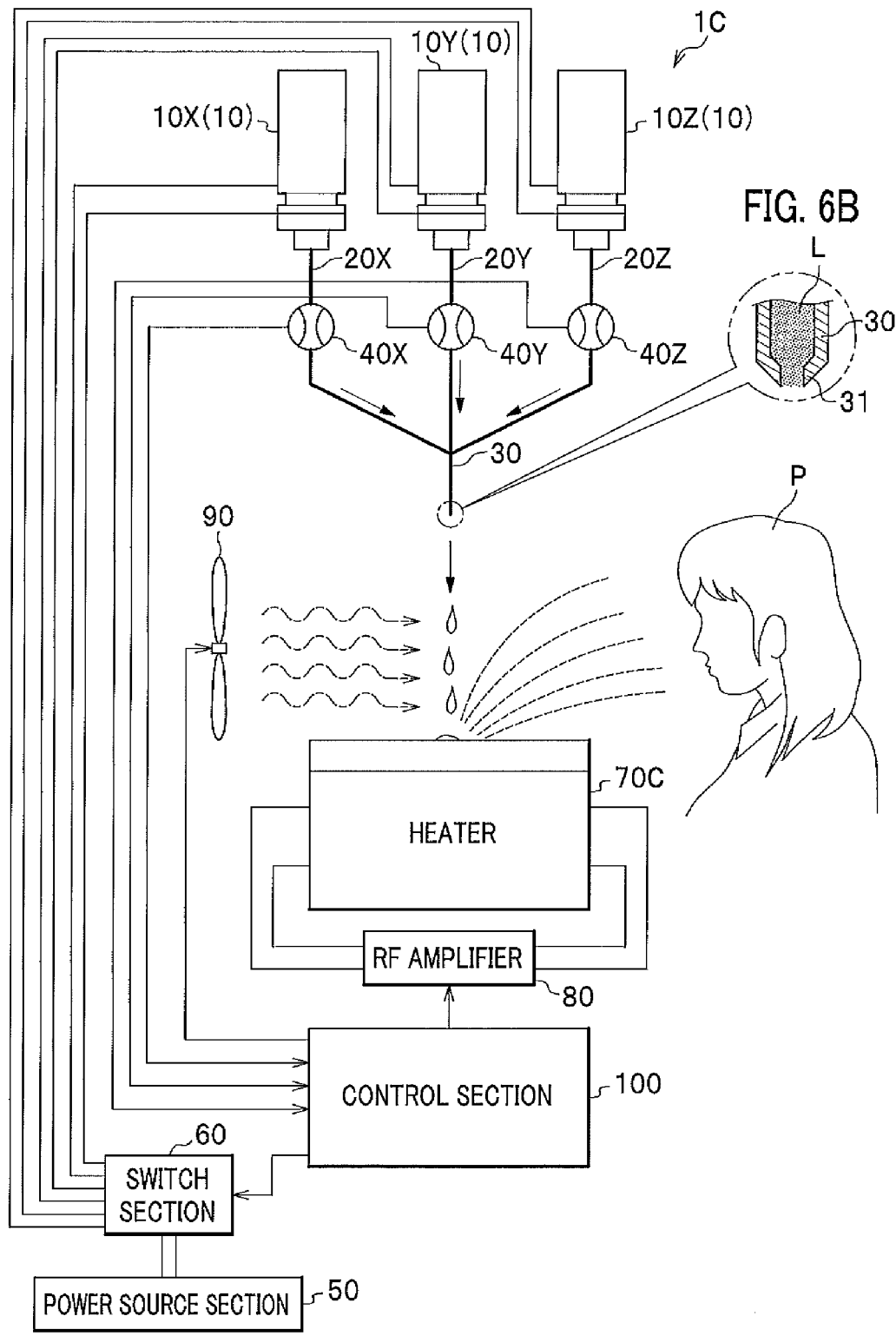
FIG. 6A is a schematic diagram of an odor generator according to a third embodiment of the present invention.
FIG. 6B is a cross section diagram of a merging pipe.

Now, description will be made of an odor generator according to a third embodiment of the present invention, with focus mainly on differences between the odor generator according to the third embodiment and the odor generator 1A according to the first embodiment, with reference to FIGS. 6A and 6B. FIG. 6A is a schematic diagram of the odor generator according to the third embodiment of the present invention, and FIG. 6B is a cross section diagram of a merging pipe.

As shown in FIG. 6A, the odor generator 1C according to the third embodiment of the present invention includes a heater 70C in place of the SAW element 70A.

The heater 70C is an example of the atomizing or vaporizing section. The heater 70C heats a liquid supplied on the surface thereof, thereby vaporizing the liquid. The heater 70C according to the present embodiment is controlled by the control section 100 to vaporize the liquids L discharged onto the surface of the heater 70C from the plurality of electroosmotic flow pumps 10X, 10Y, 10Z. The volatile fragrance ingredients volatilized and released from the vaporized liquids L are carried to the user P by the wind generated by the blowing section 90.

Figure 7:
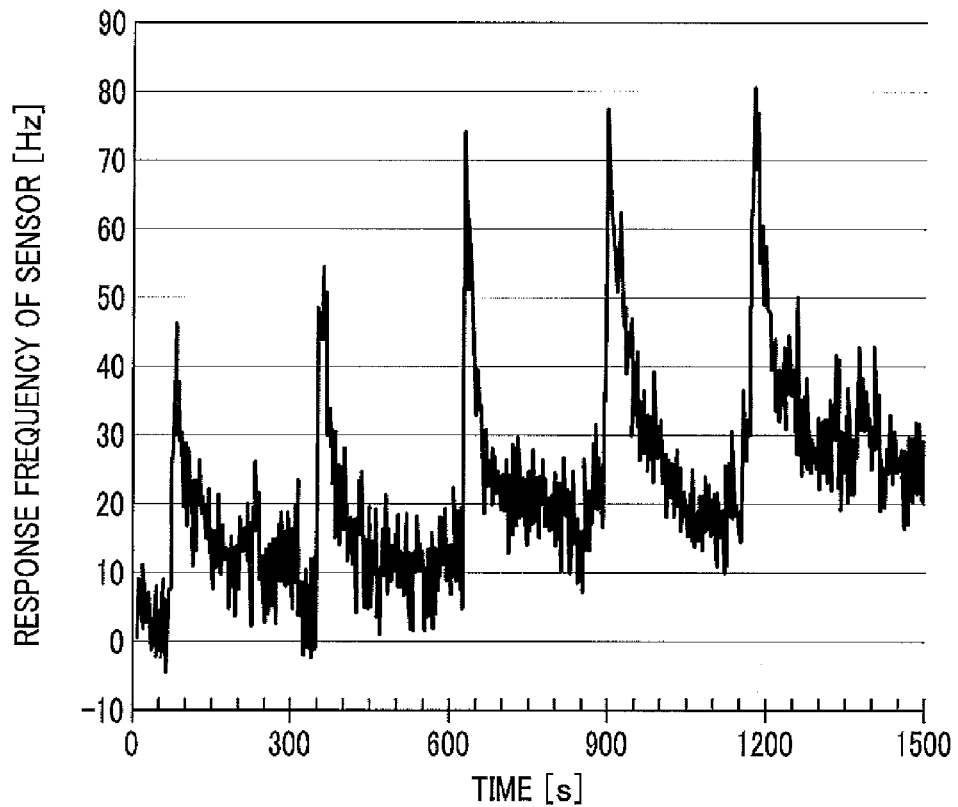
FIG. 7 is a graph representing the results of detection, by the quartz resonator gas sensor, of an odor generated by an odor generator according to a third embodiment of the present invention.
Figure 8:
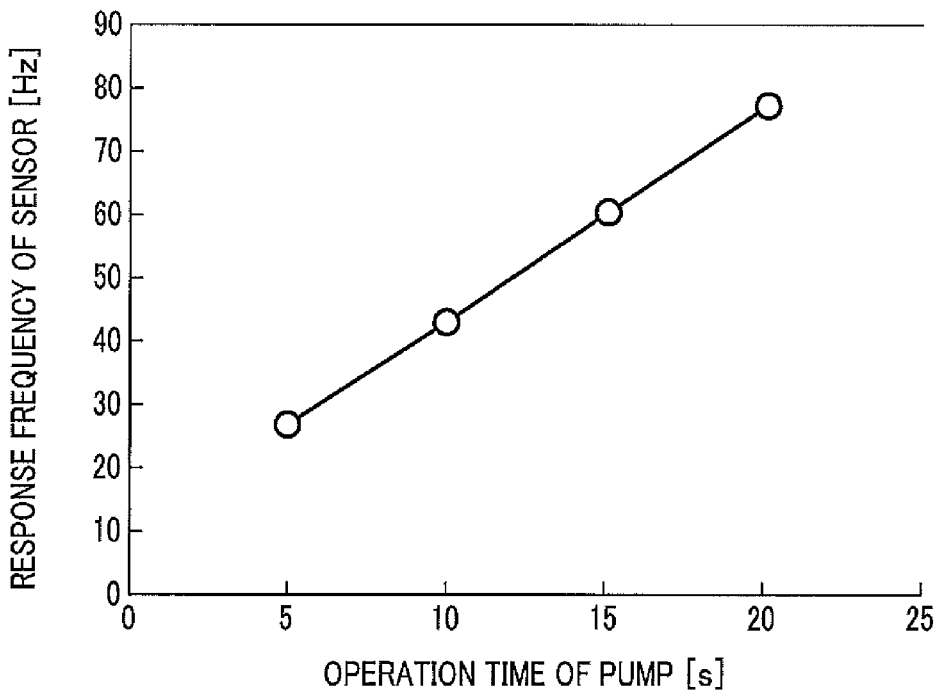
FIG. 8 is a graph representing the relationship between the operation time of an electroosmotic flow pump and the response frequency of the sensor according to the odor generator of the third embodiment of the present invention.

Now, description will be made of the operation results of the odor generator 1C according to the third embodiment of the present invention with reference to FIGS. 7 and 8. FIG. 7 is a graph representing the results of detection, by the quartz resonator gas sensor, of an odor generated by an odor generator according to the third embodiment of the present invention. The operation results of FIG. 7 were produced by vaporizing the liquid discharged from one electroosmotic flow pump 10. The odor generator according to the second embodiment of the present invention was operated with the drive voltage of the electroosmotic flow pump 10 of 24 V, the duty ratio of the electroosmotic flow pump 10 of 100%, the temperature of the heater 70B of 130° C., and the drive voltage of the blowing section 90 of 4.5 V, by using a 5% solution, by volume, of β-ionone as a low volatile fragrance ingredient in ethanol as the liquid L. The control section 100 operated the electroosmotic flow pump 10 for 10 seconds before each of the times of 70, 370, 670, 970, 1270 seconds for the liquid L to be discharged in the form of droplets onto the heater 70C at each of the times of 70, 370, 670, 970, 1270 seconds. The quartz resonator gas sensor was a sensor that had an AT-cut quartz oscillator with an oscillation frequency of 20 MHz and TCP as a sensing film. FIG. 8 is a graph representing the relationship between the operation time of the electroosmotic flow pump and the response frequency of the sensor according to the odor generator of the third embodiment of the present invention. The conditions for the results of FIG. 8 were the same as those for the results of FIG. 7 except for the operation time of the electroosmotic flow pump 10.

As shown in FIG. 7, the odor generator 1C according to the third embodiment of the present invention is capable of generating an odor immediately after the liquid L is discharged, even when a low volatile fragrance ingredient is involved. Further, the odor generator 1C is capable of stopping the generation of the odor immediately after the discharge of the liquid L is stopped.

Further, as shown in FIG. 8, according to the odor generator 1C of the third embodiment of the present invention, a proportional relationship is established between the operation time of the electroosmotic flow pump 10 and the absolute value of the response frequency of the sensor. This indicates that the concentration of an odor provided for the user P can be adjusted by adjusting the operation time of the electroosmotic flow pump 10.

Fourth Embodiment

Figure 9:
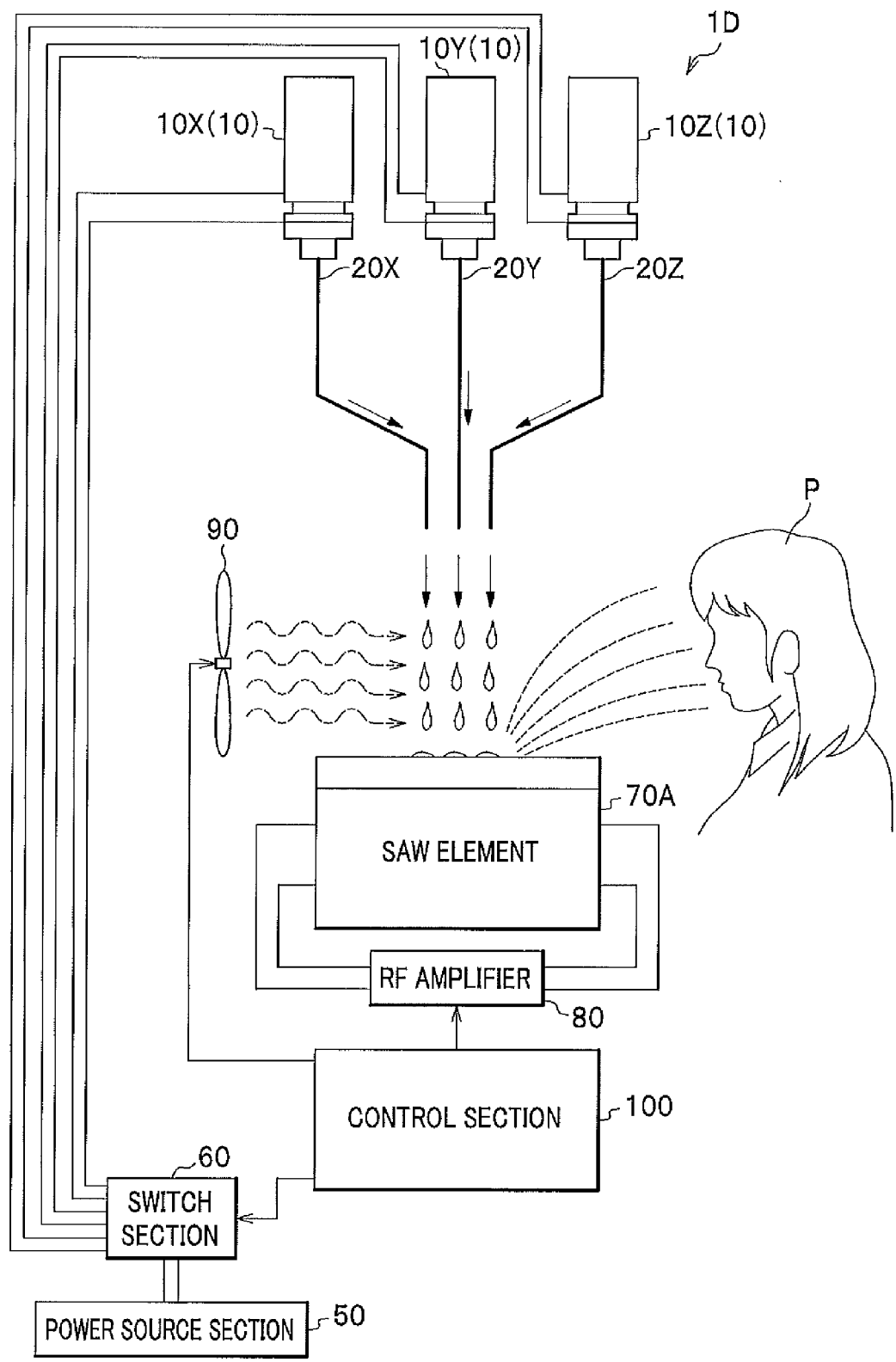
FIG. 9 is a schematic diagram of an odor generator according to a third embodiment of the present invention.

Now, description will be made of an odor generator according to a fourth embodiment of the present invention, with focus mainly on differences between the odor generator according to the fourth embodiment and the odor generator 1A according to the first embodiment, with reference to FIG. 9. FIG. 9 is a schematic diagram of the odor generator according to the fourth embodiment of the present invention.

As shown in FIG. 9, an odor generator 1D according to a fourth embodiment of the present invention includes neither the merging pipe 30 nor the plurality of liquid quantity sensors 40X, 40Y, 40Z, so that the liquids discharged from the plurality of pipes 20X, 20Y, 20Z are directly supplied onto the surface of the SAW element 70A. Here, as is the case with the merging pipe 30 of FIG. 1B, the plurality of pipes 20X, 20Y, 20Z each have a tip end provided with an orifice through which the liquid L is discharged in the form of droplets.

The odor generator 1D according to the fourth embodiment of the present invention has the same effects as the odor generator 1A according to the first embodiment.

Further, in the odor generator 1D according to the fourth embodiment of the present invention, both the plurality of liquid quantity sensors 40X, 40Y, 40Z and the feedback control by the control section 100 may be omitted.

Fifth Embodiment

Now, description will be made of an odor generator according to a fifth embodiment of the present invention, with focus mainly on differences between the odor generator according to the fifth embodiment and the odor generator 1A according to the first embodiment, with reference to FIGS. 10A and 10B. FIG. 10A is a schematic diagram of the odor generator according to the fifth embodiment of the present invention, and FIG. 10B is a cross section diagram of a merging pipe. In FIG. 10A, illustration of the power source section 50, the switch section 60 and the control section 100 is omitted.

As shown in FIG. 10A, an odor generator 1E according to a fifth embodiment of the present invention further includes a plurality of second storage sections 110X, 110Y, 110Z, 110W, a plurality of second pipes 120X, 120Y, 120Z, 120W, a second merging pipe 130, a plurality of three-way valves 140X, 140Y, 140Z, 140W, a plurality of bypath pipes 150X, 150Y, 150Z, 150W, a merging bypath pipe 160, valved flow sensors 170, 180, a filter 190, a pump 200, and an upstream pipe 210.

The plurality of second storage sections 110X, 110Y, 110Z respectively store either liquids containing different volatile fragrance ingredients or solids containing different volatile fragrance ingredients. The volatile fragrance ingredients are volatilized inside the plurality of second storage sections 110X, 110Y, 110Z. The second storage section 110W stores neither a liquid containing a volatile fragrance ingredient nor a solid containing a volatile fragrance ingredient. The second storage section 110W is for diluting the volatile fragrance ingredients to be provided for the user P.

The plurality of second pipes 120X, 120Y, 120Z, 120W are connected to the plurality of second storage sections 110X, 110Y, 110Z, 110W so that gases can flow through the plurality of second pipes 120X, 120Y, 120Z, 120W and the plurality of second storage sections 110X, 110Y, 110Z, 110W.

The merging pipe 130 is connected to the plurality of gas pipes 120X, 120Y, 120Z, 120W so that gases can flow through the merging pipe 130 and the plurality of gas pipes 120X, 120Y, 120Z, 120W. The merging pipe 130 has a tip end through which gases containing volatile fragrance ingredients can be discharged to a position over the SAW element 70A where the gases join the atomized liquids L.

The plurality of three-way valves 140X, 140Y, 140Z, 140W are disposed respectively on the plurality of second pipes 120X, 120Y, 120Z, 120W. The plurality of three-way valves 140X, 140Y, 140Z, 140W are solenoid valves controlled by the control section 100 (See FIG. 1A) to be switched between a first state in which the plurality of three-way valves 140X, 140Y, 140Z, 140W discharges the gases to a position where the gases join the liquids atomized by the SAW element 70A (the second pipes: opened, the bypath pipes: closed) and a second state in which the plurality of three-way valves 140X, 140Y, 140Z, 140W exhaust the gases into the bypath pipes 150X, 150Y, 150Z, 150W (the second pipes: closed, the bypath pipes: opened).

The plurality of bypath pipes 150X, 150Y, 150Z, 150W are connected respectively to the plurality of three-way valves 140X, 140Y, 140Z, 140W so that gases can flow through the plurality of bypath pipes 150X, 150Y, 150Z, 150W and the plurality of three-way valves 140X, 140Y, 140Z, 140W. The plurality of bypath pipes 150X, 150Y, 150Z, 150W are used to transfer the air into the plurality of second storage sections 110X, 110Y, 110Z, 110W for preventing changes in the concentrations of the gases inside the plurality of second storage sections 110X, 110Y, 110Z, 110W.

The merging bypath pipe 160 is connected to the plurality of bypath pipes 150X, 150Y, 150Z, 150W so that gases can flow through the merging bypath pipe 160 and the plurality of bypath pipes 150X, 150Y, 150Z, 150W.

The valved flow sensor 170 is disposed on the second merging pipe 130, and has a sensor and a needle valve. The sensor is for detecting and displaying the flow rate of the gases flowing through the second merging pipe 170. The needle valve is for manually adjusting the flow rate of the gases.

The valved flow sensor 180 is disposed on the merging bypath pipe 160, and has a sensor and a needle valve. The sensor is for detecting and displaying the flow rate of the gases flowing through the merging bypath pipe 160. The needle valve is for manually adjusting the flow rate of the gases.

The filter 190 is disposed on the merging bypath pipe 160, and contains activated charcoal or the like for removing odors from the gases flowing through the merging bypath pipe 160 before the gases are exhausted.

The pump 200 is controlled by the control section 100 (See FIG. 1A) to supply the air through the upstream pipe 210 into the plurality of second storage sections 110X, 110Y, 110Z, 110W. The plurality of respective second pipes 120X, 120Y, 120Z and the upstream pipe 210 are connected to upper sections of the plurality of second storage sections 110X, 110Y, 110Z so that gases can flow through the plurality of second pipes 120X, 120Y, 120Z and the upstream pipe 210 and the plurality of second storage sections 110X, 110Y, 110Z. Thus, the gases of the volatile fragrance ingredients volatilized in the second storage sections 110X, 110Y, 110Z are carried on the air supplied thereinto through the upstream pipe 210 to be introduced into the plurality of second pipes 120X, 120Y, 120Z.

The provision of an odor using the plurality of second storage sections 110X, 110Y, 110Z, 110W and the upstream pipe 210 is suitable for blending (mixing) of a number of (up to several tens of) fragrance ingredients.

In the odor generator 1E according to the fifth embodiment of the present invention, in order to generate and provide a desired odor for the user P, the control section 100 controls the plurality of three-way valves 140X, 140Y, 140Z, 140W to adjust the ratios of the periods for which the plurality of second pipes 120X, 120Y, 120Z, 120W are open (the duty ratios of the plurality of second pipes 120X, 120Y, 120Z, 120W), adjust the quantities of the gases flowing through the plurality of second pipes 120X, 120Y, 120Z, 120W, and thereby adjust the ratio of the volumes of the volatile fragrance ingredients flowing through the second merging pipe 130 to join the liquids L atomized by the SAW element 70A which is an example of the atomizing or vaporizing section, thereby generating and providing a desired odor for the user P.

According to the odor generator 1E of the fifth embodiment of the present invention, the volatile fragrance ingredients volatilized inside the plurality of second storage sections 110X, 110Y, 110Z are used as gases of intermediate to high volatile fragrance ingredients, whereas the liquids stored in the plurality of electroosmotic flow pumps 10X, 10Y, 10Z are used as ones containing low volatile fragrance ingredients, thereby generating and providing a desired odor for the user P.

While the embodiments of the present invention have been described, such description is for illustrative purposes only, and it is to be understood that changes and variations may be made without departing from the spirit or scope of the invention. For example, according to the odor generator 1E of the fifth embodiment, at least either the electroosmotic flow pumps or the second storage sections may be replaced with a single equivalent component. Further, it is to be understood that odor generators configured by combining the types of the atomizing or vaporizing sections, the structures of the pipes, the merging pipes and the like, of the odor generators 1A, 1B, 1C, 1D and 1E according to the first to fifth embodiments are also within the scope of the present invention.

DESCRIPTION OF REFERENCE CHARACTERS

1A, 1B, 1C, 1D, 1E odor generator
10 (10X, 10Y, 10 Z) electroosmotic flow pump
11 storage section
12 outlet section
12a porous material
40X, 40Y, 40Z liquid quantity sensor
70A SAW element (atomizing or vaporizing section)
70B ultrasonic vibrator (atomizing or vaporizing section)
70C heater (atomizing or vaporizing section)
100 control section
110X, 110Y, 110Z, 110W second storage section
120X, 120Y, 120Z, 120W second pipe
130 second merging pipe
140X, 140Y, 140Z, 140W three-way valve

We claim:
1. An odor generator comprising:
an electroosmotic flow pump including:
   a storage section for storing a liquid containing a volatile fragrance ingredient,
   a porous material, and
   an outlet section,
wherein the porous material is located between the storage section and the outlet section, and the stored liquid is discharged to the outlet section of the pump through the porous material when a voltage is applied to the porous material, and
an atomizing or vaporizing section for atomizing or vaporizing the liquid discharged from the outlet section,
a plurality of electroosmotic flow pumps, each electroosmotic flow pump storing a liquid containing a different volatile fragrance ingredient, respectively, and
a control section for controlling operations of the plurality of electroosmotic flow pumps, a plurality of pipes for the liquids to flow through, each pipe of the plurality of pipes is connected respectively to the outlet sections of the plurality of electroosmotic flow pumps;

a merging pipe connected to the plurality of pipes for merging the liquids flowing thereinto and allowing the merged liquids to be discharged to the atomizing or vaporizing section, and a plurality of liquid quantity sensors for detecting quantities of the respective liquids flowing through the plurality of pipes, wherein the atomizing or vaporizing section is a surface acoustic wave element, and the control section controls the operations of the plurality of electroosmotic flow pumps by feedback of detection results from the plurality of liquid quantity sensors.

2. The odor generator of claim 1, further comprising:

a second storage section for storing a liquid or a solid containing a volatile fragrance ingredient;

a pump for supplying air to the second storage section;

a second pipe connected to the second storage section for a gas inside the second storage section to flow through; and a three-way valve disposed on the second pipe and operable to be switched between a first state in which the three-way valve discharges the gas to a position where the gas joins the liquid or liquids atomized or vaporized by the atomizing or vaporizing section, and a second state in which the three-way valve exhausts the gas into a bypath.

* * * * *